United States Patent
Postrel

(10) Patent No.: US 12,280,019 B2
(45) Date of Patent: Apr. 22, 2025

(54) ANTI-AGING THERAPY FOR HUMANS AND OTHER MAMMALS

(71) Applicant: Richard Postrel, Miami Beach, FL (US)

(72) Inventor: Richard Postrel, Miami Beach, FL (US)

( * ) Notice: Subject to any disclaimer, the term of this patent is extended or adjusted under 35 U.S.C. 154(b) by 0 days.

(21) Appl. No.: 18/607,433

(22) Filed: Mar. 16, 2024

(65) Prior Publication Data

US 2024/0216295 A1 Jul. 4, 2024

Related U.S. Application Data

(63) Continuation-in-part of application No. 18/236,397, filed on Aug. 21, 2023, which is a continuation-in-part of application No. PCT/US2022/017142, filed on Feb. 21, 2022, which is a continuation of application No. 17/227,320, filed on Apr. 11, 2021, now Pat. No. 12,115,135, application No. 18/607,433 is a continuation of application No. 17/227,320, filed on Apr. 11, 2021, now Pat. No. 12,115,135, which is a continuation-in-part of application No. 15/952,226, filed on Apr. 12, 2018, now abandoned, and a continuation-in-part of application No. 15/950,230, filed on Apr. 11, 2018, now Pat. No. 10,561,118.

(60) Provisional application No. 63/151,073, filed on Feb. 19, 2021, provisional application No. 63/015,073, filed on Apr. 24, 2020, provisional application No. 62/537,027, filed on Jul. 26, 2017, provisional application No. 62/537,031, filed on Jul. 26, 2017.

(51) Int. Cl.

| | | |
|---|---|---|
| A61K 31/08 | (2006.01) | |
| A23K 20/111 | (2016.01) | |
| A23K 20/121 | (2016.01) | |
| A23K 20/184 | (2016.01) | |
| A61K 31/05 | (2006.01) | |
| A61K 31/085 | (2006.01) | |
| A61K 31/192 | (2006.01) | |
| A61K 31/352 | (2006.01) | |
| A61K 31/566 | (2006.01) | |

(52) U.S. Cl.
CPC ............ *A61K 31/05* (2013.01); *A23K 20/111* (2016.05); *A23K 20/121* (2016.05); *A23K 20/184* (2016.05); *A61K 31/085* (2013.01); *A61K 31/192* (2013.01); *A61K 31/352* (2013.01); *A61K 31/566* (2013.01)

(58) Field of Classification Search
CPC .... A61K 31/05; A23K 20/184; A23K 20/185; A23K 20/168; A23K 20/121; A23K 20/111
See application file for complete search history.

(56) References Cited

U.S. PATENT DOCUMENTS

| | | | |
|---|---|---|---|
| 8,221,809 B2 * | 7/2012 | Subramanian | A23K 20/179 426/89 |
| 9,480,689 B1 * | 11/2016 | McGlone | A61P 15/08 |
| 2018/0071314 A1 * | 3/2018 | Dunlop | A61P 15/00 |
| 2024/0043473 A1 * | 2/2024 | Wood | C07K 7/06 |

FOREIGN PATENT DOCUMENTS

WO WO-2020239784 A1 * 12/2020 ............. A61K 31/05

OTHER PUBLICATIONS

Genetically modified microbial host cell (Year: 2020).*

* cited by examiner

*Primary Examiner* — Yvonne R Abbott-Lewis

(57) ABSTRACT

The present invention discloses a system and method for preparing and delivering various precursor compositions as a replacement therapy for testosterone and other hormone deficiencies that naturally occur with aging in humans and other mammals. Precursor compositions are selected and designed for the purpose of formulating non-toxic therapeutic hormone supplement for oral consumption. The invention features low dose continuous supplementation to be incorporated with daily meals. The process of the present invention delivers an orally ingested substance, e.g., a food, supplement, etc., that contains an anti-aging formulation comprising a hormone precursor (prohormone) that is absorbed by the digestive system and secreted into the bloodstream with a second substance to facilitate its ingestion, absorption and delivery to the body's tissues.

21 Claims, No Drawings

ANTI-AGING THERAPY FOR HUMANS AND OTHER MAMMALS

CROSS-REFERENCE TO RELATED APPLICATIONS

The present application is a continuation application of U.S. application Ser. No. 17/227,320 that is a divisional application of U.S. application Ser. No. 15/952,230 and patent Ser. No. 10,561,118. Priority is claimed to related application Ser. No. 15/952,226 and provisional applications 62/537,027, 63/151,073 and 62/537,031, each of which is incorporated in entirety by reference.

BACKGROUND OF THE INVENTION

The present invention discloses a system and method for preparing and delivering various precursor compositions as a replacement therapy for testosterone and other hormone deficiencies that naturally occur with aging in humans and other mammals. Precursor compositions are selected and designed for the purpose of formulating non-toxic therapeutic hormone supplement for oral consumption. The invention features low dose continuous supplementation to be incorporated with daily meals. The process of the present invention delivers an orally ingested substance, e.g., a food, supplement, snack, etc., that contains an anti-aging formulation comprising a hormone precursor (prohormone) that is absorbed by the digestive system and secreted into the bloodstream with a second substance to facilitate its ingestion, absorption and delivery to the body's tissues.

The prohormone circulates to its site of action, a tissue or organ that processes or metabolizes the pheromone through one or more enzymatic reactions to a locally active hormone. Hormones are locally reactive when they are in contact with a receptor for that hormone. Undesired stimulation that would result from hormone circulating freely (as would occur when a hormone is injected) is avoided. Toxic build-up, e.g., in the liver, kidney, adrenal gland, etc., is avoided. In accordance with the present invention, hormonal effects occur where when and where needed, and toxic encounters of active hormone with tissues and cells along the circulatory pathway are avoided.

The delivery process for the anti-aging prohormone is enhanced by formulating the food with an accessory compound that enhances controlled uptake of nutrients by the cells that line the intestines and may stimulate appetite. (The term "food" may be used as a shorthand term for "ingestible" or "edible" unless evidenced by contrary context.) The present invention thus teaches lessening the aging process in humans and other mammals by feeding a prohormone compound combined with a cannabinoid compound. The cannabinoid compound delivered in the food activates the existing cannabinoid receptors in the gut to interact with the humans and other mammals endocrine and nervous systems to promote appetite and ingestion. In addition to stimulating appetite and ingestion, activating these receptors facilitates absorption of gut contents by intestinal cells. Absorption of the prohormone in the food is stimulated to occur with a more rapid and more controlled delivery to the bloodstream. Potential worries regarding cannabinoid effects in general circulation are minimized since the cannabinolic compounds bind to receptors on the intestinal cells and are only active there, not in general circulation.

As humans and other mammals grow and develop, their maturation processes are directed by hormonal communications between the animal's various systems. Different cells in the different systems respond to hormones differently depending on receptors on the cell's surface. The bloodstream delivers either active hormone or a precursor that is enzymatically acted upon locally to produce the specific locally active hormone compound when needed. When the circulation delivers an injected hormone, throughout the body, the hormone will act at inappropriate sites with resultant undesired or toxic results.

Humans and other mammals are large complex organisms made of trillions of cells. The various cells differentiate to take on different tasks to support survival of the organism of which the cells are members. These cells comprise highly specialized differentiated cells and less differentiated cells that might act as stem cells to produce one or more highly specialized differentiated cell. The cells differentiate to maximize their abilities for assigned tasks while leaving other essential functions to other specialized cells. The cells specialize by emphasizing certain activities and eschewing others. They do this by selective induction of the proteins the individual cell makes and uses. We categorize cells, tissues, enzymes, etc. by assigning by designating them as belonging to one of more systems—i.e., groups interacting to perform related functions.

The digestive or gastrointestinal system is one such collaboration of specialized cells. Food (and drugs) enter through the mouth before progressing through the esophagus, stomach, small intestine and large intestine before elimination. Cells lining this system secrete substances to aid digestion including, but not limited to enzymes, acids, co-factors, bicarbonate, hormones, lubricants, water, etc. Cells along the system receive food and chemical signals from digestive cells closer to the mouth. They also are in communication with other systems in the body though hormonal and nerve signaling. Cells in the digestive system both receive and send instructions to other parts of the body to facilitate absorption and delivery of nutrients to the bloodstream and then to the whole body.

The present invention provides in oral compositions absorbable and/or metabolizable hormone supplements that can be incorporated into a human's and other mammal's regular diet to invigorate metabolism and general good health. The supplemented hormone is provided in an inactive form that is available for conversion by enzymatic activity at its desired site of action to a compound that stimulates the local androgen receptor. The prohormone delivered into the bloodstream acts as a substrate compound that individual body systems or cells can use to convert to hormones with one or more activities appropriate to that specific site. Well-known prohormones include dehydroepiandrosterone (DHEA), pregnenolone, androstenedione and androstenediol.

To deliver these prohormones as a beneficial supplement to the cells, the digestive system plays a necessary role. Optimizing absorption timing and magnitude requires interaction of multiple body systems. As we and all mammals age these signaling pathways break down, thereby reducing optimal performance, health and general well-being. Providing supplements to replace the hormones whose production is reduced may be beneficial in itself. But imperfections in the intestinal uptake mechanisms reduce or skew beneficial effects; and the hormone being in a form highly active across a number of cells with receptors therefore will exert undesired, potentially toxic effects.

In accordance with the present invention, absorption from the gastrointestinal tract is facilitated in both timing and magnitude by utilizing the body's extensive endocannabinoid receptor signaling system.

Several types of cannabinoid receptors can be found in cells throughout the body. The gastrointestinal system employs several cannabinoid receptors, most commonly members of the

SUMMARY OF THE INVENTION

The present invention provides in oral compositions absorbable and/or metabolizable hormone supplements that can be incorporated into a human's and other mammal's regular diet to invigorate metabolism and general good health. The supplemented hormone is provided in an inactive form that is available for conversion by enzymatic activity at its desired site of action to a compound that stimulates the local androgen receptor. The prohormone delivered into the bloodstream acts as a substrate compound that individual body systems or cells can use to convert to hormones with one or more activities appropriate to that specific site. Well-known prohormones include dehydroepiandrosterone (DHEA), pregnenolone, androstenedione and androstenediol.

To deliver these prohormones as a beneficial supplement to the cells, the digestive system plays a necessary role. Optimizing absorption timing and magnitude requires interaction of multiple body systems. As we and all mammals age these signaling pathways break down, thereby reducing optimal performance, health and general well-being. Providing supplements to replace the hormones whose production is reduced may be beneficial in itself. But imperfections in the intestinal uptake mechanisms reduce or skew beneficial effects; and the hormone being in a form highly active across a number of cells with receptors therefore will exert undesired, potentially toxic effects.

DETAILED DESCRIPTION OF THE INVENTION

In accordance with the present invention, absorption from the gastrointestinal tract is facilitated in both timing and magnitude by utilizing the body's extensive endocannabinoid receptor signaling system.

Several types of cannabinoid receptors can be found in cells throughout the body. The gastrointestinal system employs several cannabinoid receptors, most commonly members of the class G-Protein-coupled Receptors (GPR or GPCR) transmembrane proteins. These receptors span the plasma membrane and interact with a GTP-coupled internal protein when stimulated extracellularly. Cannabinoid receptors, CB1 and CB2 are two well-known members of this class. Numerous additional GPRs or GPCRs have now been shown to bind cannabinolic ligands. GPR55 and PPARα are additional examples of endocannabinoid receptors with digestive activities.

The oral composition comprises a selected prohormone and may be orally delivered by any suitable means, including, but not limited to: as a toothpaste, feed, a spritz, a small snack or treat, a food formulation, a food supplement, a prescription food product, a reward, a spray, an ampule, a chew toy, a supplemented rawhide, a chewable edible, etc.

Several types of cannabinoid receptors can be found in cells throughout the body. The gastrointestinal system employs several cannabinoid receptors, most commonly members of the class G-Protein-coupled Receptors (GPR or GPCR) transmembrane proteins. These receptors span the plasma membrane and interact with a GTP-coupled internal protein when stimulated extracellularly. Cannabinoid receptors, CB1 and CB2 are two well-known members of this class. Numerous additional GPRs or GPCRs have now been shown to bind cannabinolic ligands. GPR55 and PPARα are additional examples of endocannabinoid receptors with digestive activities.

The oral composition comprises a selected prohormone and may be orally delivered by any suitable means, including, but not limited to: as a toothpaste, feed, a spritz, a small snack or treat, a food formulation, a food supplement, a prescription food product, a reward, a spray, an ampule, a chew toy, a supplemented rawhide, a chewable edible, etc.

The invention also provides methods of making the oral composition into one or more ingestible delivery devices.

While testosterone and similar androgenic supplementations have seen significant use in body builders as a muscle growth and retention booster in humans, results have been capricious with significant detrimental side effects, at least partially due to unpredictable intestinal absorption and the untargeted metabolism in tissues throughout the body. Detrimental effects have been recognized in many organs, including, but not limited to: liver, kidney, heart, etc. Abnormal cholesterol and other blood lipids, weakened immune system response and autoimmune reactions, hypertension, and severe acne are recognized effects from short term and long term use of these substances. Use of testosterone and similar steroids is recognized as unsafe leading to prohibition by many sports bodies, including, but not limited to: Major League Baseball, the NFL, the International Olympics and Para-Olympics, the NCAA, and numerous other regulatory groups. Detrimental effects are noted in animals also. Horses, for example, are tested at all major tracks for use of banned steroid substances. Testosterone and related steroids are listed as Schedule III in the US Controlled Substances Act.

Two problems are recognized with steroid supplementation: a) variable absorption and delivery to the blood dependent on dietary, environmental, behavioral, and genetic factors; and b) uncontrolled delivery and activity throughout the body, i.e., to tissues with current need—as well as tissues where current steroid activity will be counterproductive. While scheduled injections can overcome the absorption inconsistencies, constant injections,—one or more times a day—is not generally feasible. The inconsistent, highly variable sites of action of the active hormone mask beneficial actions as the hormone acts throughout the body including numerous locations where it is not needed. The present invention obviates the use of injections through improved and more predictable absorption and delivery of a steroid hormone precursor in conjunction with a cannabinoid component. Less psychoactive cannabinoids are preferred so that activity levels are merely increased, not greatly (and possibly unpredictably) changed. However, the doses required for enhanced uptake might be considered negligible in comparison to some of the "edibles" available in states where *cannabis* is legal.

The improved controlled delivery of the pro-androgenic stimulant to the bloodstream and deposition at desired locations in the body where local enzymes are in control for activation, decreases the potential for side-effect damage to the liver, kidneys, adrenal, and other organs or systems. Controlled uptake by the intestines minimizes the time that the gut microbiome changes the chemical makeup of the supplemented compound(s) leading to more targeted and predictable androgenic effects. When a cannabinolic oil or alcohol is used, additional oils, including, but not limited to: vegetable, rapeseed/canola, soy, corn, peppermint, lavender, sandalwood, bergamot, rose, chamomile, ylang-ylang, tea tree, myrcene/hops, jasmine, lemon, etc. may be preferred to improve flavor, but also as a carrier for the supplemented active ingredients. The prohormone and/or cannabinolic supplement compound may be provided as an ester or other modified format to facilitate packaging, shelf-life, delivery to desired portion of the gastrointestinal tract, etc. DHEA is a prohormone for both testosterone and estrogen allowing the body's tissues to process the supplement in the tissues to outcomes specific to the organism and the tissue. DHEA has been approved by the FDA for use by humans. 7-keto-DHEA, and DHEA-S, both naturally occurring metabolites of DHEA, are alternative compounds that may substitute for DHEA or be co-administered. FDA approval is strong endorsement of the safety potential of DHEA precursor hormone.

Anabolic steroids, a class of steroids that includes androgenic compounds such as testosterone and prohormones, e.g., dehydroepiandrosterone (DHEA), pregnenolone, androstenedione, androstenediol, etc., are the steroids known for use by athletes to stimulate growth, increase strength, and allegedly improve athletic performance. These, and in fact all anabolics (steroids or other compounds binding androgen receptors and promote growth), are in a group associated with serious side effects and must be used sparingly, and most definitely not in the extreme doses used in the past by athletes. Steroid use is severely restricted in international competitions, because of the unfair increased strength with less training, but also because of the observed long-term health damage, including, but not limited to: hepatic, endocrine, and reproductive function; tumors of the liver and kidneys; cardiac abnormalities; and psychiatric symptoms.

Careful and predictable controlled administration of steroid supplementation thus is a concern. Cannabinoids, while themselves being banned in sports (as performance enhancing drugs), are not considered deleterious to human or animal health when cautiously administered or taken.

The endocannabinoid system (ECS) is an important lipid based signaling and immunomodulator system. Lipophilic compounds, those that can readily cross plasma membranes are prime activators of these endocannabinoid pathways. Research relating to medical uses of marijuana and traditional medicines has shown that at least compounds that bind CB1 and CB2 participate in modulating many physiological responses including, but not limited to: appetite, respiration, metabolism, transmembrane stimulation, nutrient uptake, inflammation, allergy, pain, neurotransmission, etc. The ECS is comprised of G-protein coupled receptors (GPCRs) including, but not limited to human: CB1, CB2, TRPV1, TRPV2, TRPV3, TRPV4, TRPA1, TRPM8, GPR55, GPR118, GPR119, etc. and the animal homologues of similar activity but sometimes different names. The present invention incorporates beneficial effects of cannabinoids, especially the anti-inflammatory, nutrient uptake, and metabolic enhancement effects, to stimulate and predictably control prohormone uptake by intestinal cells.

The native cannabinoid receptor ligands aka "endocannabinoids" are classically represented by arachidonylethanolamide (anandamide, AEA) and 2-arachidonoylglycerol (2AG). Tissue levels of endocannabinoids are maintained by the balance between biosynthesis (e.g., phospholipase D and diacylglycerol lipase-dependent and other pathways), cellular uptake and degradation by enzymes principally, but not limited to: fatty acid amide hydrolase (FAAH) and/or monoacylglycerol lipases (MAGL). Since the discovery of CB1 and CB2 GPCRs such as GPR18, GPR55, GPR119 and the TRPs have been recognized as members of the cannabinoid family.

Two notable catabolic enzymes, fatty acid amide hydrolase (FAAH) and monoglycerol lipase (MAGL), are involved in the breakdown of anandamide and 2AG, respectively. Simply put, less FAAH and MAGL means more AEA and 2AG. So, inhibitors of these catabolic enzymes, for example, by nutmeg extracts, may be incorporated into supplements or foods of the present invention to raise active the levels of AEA and 2AG and to generally boost cannabinoid receptor signaling. FAAH and MAGL inhibition therefore can be effective in improving food uptake, but also in reducing or managing pain, anxiety, hypertension and various inflammatory conditions. Nutmeg extracts and food substances of similar activities are therefore optional components for inclusion in the products of the present invention.

The "cannabinoid" (a term indicating *cannabis*-like activity) compounds have diverse effects, including most notably, some psychoactive effects, became known as phyto-cannabinoids based on their similarities to compounds found in the *cannabis* genus. The endo/phyto-cannabinoids include but are not limited to: N-acylethanolami(n/d)es which include N-arachidonoylethanolamine (better known as anandamide or more simply AEA), N-palmitoylethanolamine (PEA), N-linoleoylethanolamine (LEA) and N-oleoylethanolamine (OEA).

Since living organisms share many common metabolic paths and features many mammalian endocannabinoids can be found in other species, including plant species. For example, OEA and LEA are in cocoa; black truffles when grown under certain circumstances contain high levels of AEA. Naturally sourced minimally processed cannabinoids, extracted cannabinoids, modified cannabinoids, and synthetic cannabinoids may be selected for use in the present invention. For example, some people prefer organic or natural components for themselves and/or their animals.

Maintaining AEA activity and preventing its metabolism to damaging inflammatory substances is a powerful tool. COX inhibition can limit prostaglandin D2 ethanolamide formation. A selective COX inhibitor is one approach when constraints are preferred or when other COX-1 or COX-2 pathways are favorably spared. The CDHR3 downstream effects can also be maintained with FAAH inhibition. In many examples both COX inhibition and FAAH inhibition are used.

Phytochemicals (substances found in plants or derivatives of the plant chemicals) or the plants themselves, have been recognized to possess biological activities in traditional medical practices. Several classes of compounds with similarities in structure and/or activities to the THC purported active ingredient of the marijuana source plant have been identified. These are available in several plants outside the *Cannabis* genus and can be, cultured (e.g., through selective breeding or genetic engineering), extracted, purified or synthesized chemically de novo or from derivatives. Such compounds including, but not limited to:

Cannabigerol class: cannabigerolic acid (CBGA) (antibiotic); cannabigerolic acid monomethylether (CBGAM); cannabigerol (CBG) (antibiotic, antifungal, anti-inflammatory, analgesic); Cannabigerol monomethylether (CBGM); cannabigerovarinic acid (CBGVA); Cannabigerovarin (CBGV).

Cannabichromene class: Cannabichromenic acid (CBCA); Cannabichromene (CBC) (antibiotic, antifungal, anti-inflammatory, analgesic); Cannabichromevarinic acid (CBCVA); Cannabichromevarin (CBCV); Cannabidiolic acid (CBDA) (antibiotic); Cannabidiol (CBD) ((antioxidant, anxiolytic, antispasmodic, anti-inflammatory, analgesic); cannabidiol monomethylether (CBDM); cannabidiol C4 (CBD-C4); cannabidivarinic acid (CBDVA); cannabidivarin (CBDV); cannabidiorcol (CBD-C1); $\Delta^9$-tetrahydrocannabinolic acid A (THCA-A); $\Delta^9$-tetrahydrocannabinolic acid B (THCA-B); 6a, 10a-trans-6a,7,8,10a-tetrahydro-6,6,9-trimethyl-3-pentyl-6H-dibenzo[b,d]pyran-1-ol, ($\Delta^9$ tetrahydrocannabino-, THC) (analgesic, antioxidant, antiemetic, anti-inflammation); $\Delta$9-tetrahydrocannabinolic acid-C4 (THCA-C4); $\Delta^9$-tetrahydrocannabinol-C4 (THC-C4); $\Delta^9$-tetrahydrocannabivarinic acid (THCVA); $\Delta^9$-tetrahydrocannabivarinic (THCV); $\Delta^7$-cis-isotetrahydrocannabivarin; $\Delta^9$-tetrahydrocannabiorcolic acid (THCA-C1); tetrahydrocannabiorcol (THC-C1).

$\Delta^8$-tetrahydrocannabinol class: $\Delta^8$-tetrahydrocannabinolic acid ($\Delta^8$-TCA); $\Delta^8$-tetrahydrocannabinol ($\Delta^8$-THC).

Cannabicyclol class: cannabicyclol (CBL); cannabicyclolicacid (CBLA); cannabicyclovarin (CBLV).

Cannabieson class: cannabiesoic acid A (CBEA-A); cannabiesoic acid B (CBEA-B); cannabieson (CBE).

Cannabinol and cannabinodiol class: cannabinolic acid (CBNA); cannabinol (CBN); cannabinol methylether (CBNM); cannabinol-C4 (CBN-C4); cannabivarin (CBV); cannabinol-C2 (CBN-C2); cannabiorcol (CBN-C1); cannabinodiol (CBND); cannabinidivarin (CBDV).

Cannabitriol class: cannabitriol (CBT); 10-Ethoxy-9-hydroxy-$\Delta$-6a-tetrahydrocannabinol (10-EHDT); 8,9-dihydroxy-delta-6a-tetrahydrocannabinol (8,9-DHDT); cannabitriolvarin (CBTV); ethoxy-cannabitriolvarin (CBTVE).

Miscellaneous class: dehydrocannabifuran (DCBF); cannabifuran (CBF); cannabichromanon (CBCN); cannabicitran (CBT); 10-oxo-$\Delta$-6a-tetrahydrocannabinol (OTHC); $\Delta^9$-cis-tetrahydrocannabinol (cis-THC); 3,4,5,6-tetrahydro-7-hydroxy-$\alpha$-$\alpha$-2-trimethyl-9-n-propyl-2,6-methano-2H-1-benzoxocin-5-methanol (2H-iso-HHCV); cannabiripsol (CBR); Trihydroxy-$\Delta^9$-tetrahydrocannabinol (triOH-THC).

LEA, PEA and OEA will bind to one or more of the endogenous cannabinoid receptors, but they are also important because they maintain AEA activity through their inhibition of the FAAH enzyme that is responsible for degrading AEA. N-alkylamides exert selective effects on the CB2, and have been shown to exert anti-inflammatory effects similar to AEA. *Echinacea* contains multiple N-alkylamides that have mimetic effects.

Phytoalkanes, another class of chemical compounds found in various plants, also have demonstrated cannabinolic modulation traits, e.g., n-alkanes ranging from C9 to C39, 2-methyl-, 3-methyl-, and some dimethyl alkanes are common in spices such as curcumin. The major alkane present in an essential oil obtained by extraction and steam distillation was the n-C29 alkane nonacosane (55.8 and 10.7%, respectively). Other abundant alkanes were heptacosane, 2,6-dimethyltetradecane, pentacosane, hexacosane, and hentriacontane. Curcumin reduces liver fibrosis by modulating cannabinoid receptor transmission.

In general, many plant species, especially those used for spices have anti-allergy/anti-inflammatory activities. E.g., nutmeg interacts with the endocannabinoid system by inhibiting certain key enzymes that catabolize (break down) the two main endocannabinoids, anandamide and 2AG.

β-caryophyllene, a phytocannabinoid, and/or its oxides act as full agonists of the CB2-receptor where they exert anti-inflammatory and analgesic effects that are mediated through CB2, but not CB1. Another phytocannabinoid, salvinorin A, from the plant species *Salvia divinorum* extract is a terpenoid that interacts with a cannabinoid receptor, not yet characterized that apparently forms only in inflammatory conditions. This uncharacterized receptor also acts as a κ-opioid receptor. Many sages produce similar compounds with some activity, but whose activities have not been followed in detail to identify receptor interactions. Myrcene is a major constituent of the essential oil of hops and appears to be related to opioid "high" possibly by agonizing opioid receptors or possibly by antagonizing opioid degradation. Plant sources are hops, verbana and *cannabis*. Myrcene is also found in lemongrass, thyme and mango. *Echinacea* contains multiple N-alkylamides that have cannabinoid mimetic effects.

The *Helichrysum umbraculigerum*, aka woolly umbrella *Helichrysum* or kerriekruie in Afrikaans, is a fast growing perennial herb with a strong mood-stabilizing and anti-depressant effect due to high concentrations of cannabigerol (CBG). Liverwort contains large amounts of perrottetinenic acid, a THC mimetic that binds CB1. The cacao plant has endocannabinoid activity by deactivating the FAAH enzyme thereby maintaining AEA levels and levels of similarly active fatty acid derived molecules. FAAH inhibition combines anti-inflammatory effects of several N-acylethanolamines while it targets additional receptors such as TRPV1 and peroxisome proliferator activated receptors.

While synthetic cannabinoids should be used with care in frequency and volume of dosing, one characteristic of the cannabinolic systems is that they are fantastic self-regulators. For example, exogenous AEA and similar phytocompounds that bind endogenous receptors set in motion pathways to rebalance and restore cannabinoid metabolisms including related pathways for inducing receptors synthetic enzymes and even the degradative enzymes. Small frequent doses can be all the organism requires for superbly balanced cannabinolic controls.

Testosterone, a primary anabolic steroid, is metabolized into dihydrotestosterone in the body by the 5-α-reductase (5AR) enzyme (dihydrotestosterone is thus a metabolite of testosterone). Nandrolone is a byproduct of the aromatization (conversion) of testosterone into estrogen. Testosterone is an intermediate in natural synthesis of anabolic steroids, e.g., DHT and nandrolone. As discussed above, there are serious downsides to administering testosterone as an injected or ingested metabolic supplement.

Testosterone itself is the principal male sex hormone. Hormones are defined and classified as chemical messengers of the human body, which means that hormones are what carry messages to different cells and tissues in the body to tell those cells and tissues what to do (grow muscle tissue, heal and repair, manufacture important components, perform a specific job, etc.). Without hormones of all different types, all functions within the human body will proceed unregulated and out of control. How much testosterone the average male produces is dependent on many different factors, which include: individual genetics, age, lifestyle habits, nutritional habits, and activity levels. On average, it has been determined that the median level of testosterone production among 30 year old human ~150-175 lb. males is between 50-70 mg weekly. Where any given individual might land within that range is dependent on the aforementioned factors. It is common knowledge that the most prominent effects of the hormone testosterone appear and are experienced during puberty, which is evidenced by an increase in testosterone production and secretion, and will typically reach the highest endogenous levels at this point in any given man's life. This significant increase in testosterone serves to impart very important physiological changes of the male body. Testosterone governs many different functions within the body. The nature of hormones in the circulation is to govern systemic functions remotely around the body, and testosterone is no exception to this. Dosing can be based on the blood levels of the intended recipient, their weight, the chemical nature of the supplement (bioavailability, half-life, partitioning in body compartments, binding to proteins, etc.) to maintain the animal at an androgen level approximating or preferably exceeding by about 1.5, 2, 2.5 or 3 times the previous average levels while concurrently restoring previous healthful activities.

Androgens such as testosterone and DHT bind to androgen receptors (ARs) in cells. The resulting androgen-receptor complex regulates gonadotropin secretion and spermatogenesis. The androgen-receptor complex is responsible also for external vinilization and for most androgen actions during sexual maturation and adult life. DHT is an especially potent androgen because it binds with greater affinity to androgen receptors than testosterone does. Testosterone production in intact mammals is stimulated by luteinizing hormone (LH). It is understood that follicle stimulating hormone (FSH) stimulates testosterone production also. Testosterone concentrations in the blood serum are regulated in part by a negative-feedback pathway in which testosterone inhibits the formation and/or secretion of luteinizing hormone-releasing hormone (LHRH). LHRH acts to stimulate secretion of LH by the pituitary gland. Testosterone acts also by regulating the sensitivity of the pituitary gland to LHRH.

The present invention provides improved health and longevity for well-being that can support oxytocin levels. Oxytocin is one of the natural inducers of AEA synthetic pathways. Thus, improving activities that lead to oxytocin release in the body can have a beneficial side-effect of supplementing cannabinoid production and circulating levels.

Humans and other mammals exhibit large differences in their mitochondria and mitochondrial activities. These differences may be exacerbated with aging. By optimizing energy metabolism through monitoring and improvement in mitochondrial metabolism, (energy efficiency) the vitality effects observed through androgen balancing may be further enhanced. Accordingly, the invention may include an augmented approach wherein, in conjunction with androgen balancing as an anti-aging measure that optimizes activities and/or in conjunction with system rebalancing by enhancing cannabinoid activities, additional improvement may be obtained by also optimizing mitochondrial activity, metabolism and performance.

Common diseases in aging include: arthritis, which reduces activity levels and may make the subject more irritable or reclusive; obesity, which can acerbate arthritis and other diseases such as cardiomyopathy and usually reduces activity levels; joint dysplasia, which reduces comfort and activity; gum disease; diabetes; blindness of various etiologies; dementia; and other diseases of aging familiar in humans and other mammals. Metabolic functions may be impaired, for example, adipose tissue may experience accelerated or location improper deposition and/or aberrant utilization, glucose metabolism and metabolism of other sugars may be altered though diabetic effects and compensating metabolic shifts.

For example, in humans both free testosterone and total testosterone have been documented in their decline as a male ages. Up to their fifties, human males essentially maintain total testosterone with about a 25% drop in free testosterone from about the age of thirty to about fifty. In the ensuing years both total and free testosterone continue to decline until about the age of eighty the levels are only about half the levels previous to age fifty. While there are differences in effects of aging between mammals, in general testosterone levels decline with age as the animal's vitality also declines. As an approximation, 25% supplementation may be used as augmentation beginning at approximately age 5 in dogs and age 7 in cats. The supplemented amounts will depend on the androgen compound chosen and its comparison in activity to testosterone. Advisedly testosterone levels will continue to be monitored with additional supplementation as Testosterone activity lessens.

Evidence is building that age related reduced testosterone levels in human males, and thus in other mammals, may be related to growth of pot bellies and possibly, heart attacks, strokes, osteoporosis, clinical depression and some presentations of Alzheimer's disease.

Evidence relating to human females suggests that testosterone levels may be important with regard to depression, activity level and general sense of well-being. There is also evidence that in human females, a testosterone supplement may improve activity levels and maintain a leaner body. Low testosterone levels in human females have been associated with lack of motivation and a sense of fatigue. The common weight gain and increased adipose tissue deposition in women starting approximately 10 years prior to menopause coincides with a commonly observed decreased level of circulating testosterone. This suggests an important component of the present invention relating to maintaining testosterone balance will benefit both male and female organisms.

Studies suggest that maintaining an optimized testosterone level as the humans or other mammals age can result in improved vigor, reduced injury, and greater activity and possibilities for social interaction. Testosterone is often chested as a marker for steroid hormones generally. Management of circulating testosterone also has the possible effect of preventing or reducing injury, such as muscle or joint injury, and can thereby appear as an anti-aging agent to maintain a higher level of activity available to the individual. Effective supplementation in accord with the present invention should result in multiple positive effects throughout the entire body.

While "testosterone" level management and supplementation where warranted have proved successful in improving specific health effects all over the body, administration has been carefully controlled within the medical community to avoid misuse and deleterious effects that can be associated with elevated testosterone levels that exceed safety limits.

The observation that as testosterone levels decrease during aging and that testosterone is believed to enhance muscle development suggests that the occurrences are not purely coincidence. In fact, muscle tissue expresses androgen receptor (AR) protein so it would be understood that testosterone would influence muscle metabolism. Supporting evidence that testosterone supplementation or replacement increases muscle fiber protein synthesis and that pluripotent stem cells capable of differentiating into muscle fiber cells have high levels of AR expression suggests a causal relationship exists. Accordingly, Supplementing androgen, e.g., testosterone to an aging animal may maintain or build muscle mass. Better muscle mass is associated with lower incidences of diabetes so the benefits of testosterone balancing would be expected to cascade through many organs and tissues. But at lower levels of activity while testosterone balance may produce profound benefits an even greater improvement is possible if mitochondrial optimization is partnered with the balancing.

Androgenic compound abusers have contributed to testosterone's and other androgenic hormones' shocking disparagement in the news and social media through reports of occasional wild and violent activities. There are also reports of severe health outcomes such as brain tumors, but perhaps, partly related to publicity from these warnings about androgenic misuse and exhibits of "over manliness", steroid supplementation/abuse continues in a significant segment of the population, both male and female. Though abuse may present long term problems for the individual and society, society at large, law enforcement, and politicians can understand that the abuse is a result of testosterone's positive effects.

While some desired effects, for example, increased muscle mass in body builders and other professional athletes, may be valued for their immediate effects, long term effects, for example use over decades, has been shown to increase propensity for heart attack and stroke. The length of administration and the expected remaining lifespan of the individual should be considered before enhancing androgen in the bloodstream.

Other noted effects include elevated LDL and higher LDL/HDL ratio, increased blood pressure, increased cancer, for example, brain and liver, and difficulty in movements that may be caused by excess tissue deposition. Androgen abuse is also associated with testicular wasting or atrophy which in humans may or may not be desired depending on one's desires for fatherhood. In neutered dogs, this of course would not be a relevant concern.

Most of these recognized problems can be avoided or minimized simply by managing testosterone blood levels to levels more prevalent in normal animals or limiting administration to older animals with for example an expected remaining lifespan of about a decade or less. For example, the irritability, aggressive behaviors, rage, violence, delusions, manic eating, etc., appear to be associated with abuse of androgens that involves massive dosing regimens; liver disease and tumor events appear associated with long term administration of moderate to high doses.

The present invention seeks to avoid these problems often associated with aging by optionally providing systems wide rebalancing tools in the form of cannabinolic augmentator supplements or facilitators and by monitoring, either through feeling of well-being, behavioral observation, or potentially by measuring blood, saliva, urine, or skin, androgen or androgenic activity. The reliance on the prohormone minimizes system wide inappropriate effects. Unless behavioral problems become evident testing of blood may not be necessary or recommended.

Restoration of testosterone (as a marker for steroid hormones) to approach normal physiological levels can help to restore to a more youthful state and improve the function of many of the different systems where testosterone's effects on the cellular level are accomplished. This includes, for example, action in the bone marrow that increases red blood cell count, which translates to increased endurance, improvement in energy, well-being, and restoration of muscle mass.

There are various studies that have determined where, on average, testosterone levels should be in males according to various age groups. Generally, testosterone in human males declines about 1% per year from the late thirties. For animals, the decline may be steeper depending on size, species and lifespan, and will generally occur at a younger but still at a middle age.

Supplementation in accordance with the present invention may help avoid serious medical problems in pets. For example, osteoarthritis and hip dysplasia are especially common and problematic in larger dog breeds and larger dogs in general. Dogs will reduce activity level and avoid some previous activities to hide the symptoms or to avoid associated pain. Aging is also associated with a general lethargy that can be a result of or mask other diseases such as a failing heart, painful joints, decreased muscle tone, arthritis, etc. and may be a factor in weight gain that can cause or exacerbate other disorders. Increased dysplasia and obesity have been observed to have increased occurrence in canines that have been spayed or neutered. While the benefits, in most cases, necessity of spaying or neutering are profound, the procedure does remove a major source of androgenic hormone, testosterone and its metabolites, from the animal's physiology. While other organs such as the adrenal produce androgens, often the amount decreases as the animal ages and becomes insufficient for optimizing animal activity and health. Similar concerns prevail in cats, but may be less noticed. Vigilance is advised.

Human and other mammalian bodies, like those of dogs, cats, rabbits, etc., have internal means of messaging. Blood flow can be increased or decreased to an area or organ. Nerves sense what is happening at different locations within the body and then transmit information to the central nervous system where multiple inputs are analyzed and coordinated to initiate an output. The output could be neurotransmitter secretion causing a nerve impulse sending instructions to another location in the body. Another very important means of internal commutation is the endocrine system which uses hormones as signaling agents. Hormones are chemicals just as neurotransmitters, but hormones have effect distant from the place of release.

Hormones are chemical messengers used to transfer information through the bloodstream from one part of the body, generally an endocrine gland, to the body in general or to a specific target organ that has a receptor capable of binding or receiving the hormone. Target organs have specialized receptors that gather information that has been transferred from the circulatory system by hormones. An example of a target organ is the uterus, which is stimulated by the circulating hormone estrogen to develop uterine glands. Hormone production—for example, testosterone, estrogen, and progesterone—is regulated by another hormone secreting endocrine gland, the pituitary, at the base of the brain.

Prohormones are building block chemicals used to produce the resultant hormones. In general, the blood levels of sex steroid prohormones are not regulated by any one factor. They are removed from circulation when they bind one of the cells expressing their receptor protein. In contrast, prohormones are generally available to assist in the production of hormones at a site in need that is stimulated by messages in the organism to bind and activate the prohormone, which then act locally or as chemical messengers to other target organs. Injecting a functioning hormone eliminates the problem that may stem from insufficient prohormone, but undermines the natural feedback controls of the body. Increasing circulating prohormone in accord with the present invention thus can result in more balanced supplementation.

The present invention is based in part on the insight that administering one or more androgenic hormones or prohormones to generally healthy appearing animals can increase their overall health and beneficial interactions with nearby humans. In addition, though not as readily observable, achieving an optimal level of circulating hormone may be associated with an increased quality of life, possibly through enhancement of the immune system's ability to defend against bacteria and viruses, to resist cancer, to enhance the circulatory system, and/or to ameliorate undesired stress-responses. Co-administration of compounds active in the cannabinolic systems fine-tunes and facilitates such administrations.

DHEA, a compound with FDA approval for use in humans, is a preferred prohormone for inclusion in products of the present invention. DHEA, aka androstenolone, is an endogenous steroid hormone precursor produced mostly in the adrenal glands, but also in gonads and brain tissue. DHEA is converted to DHEA 3β-sulfate (DHEA-S) by sulfation at the C3β position by the sulfotransferases SULT2A1 and SULT1E1 DHEA-S is more stable in circulation, present in amounts perhaps 250 to 300 times DHEA. DHEA-S thus acts as a reservoir or sink for long term availability of the prohormone. DHEA-S is retro-converted back into DHEA in target peripheral tissues by steroid sulfatase. DHEA/DHEA-S is the most abundant circulating steroid measured in humans. The circulating DHEA serves as a substrate for biosynthesis of androgen and estrogen steroids in the gonads and many other tissues. Potential biological effects of DHEA are reduced by the natural conversion to DHEA-S. DHEA therefore can be fed or supplemented without serious concerns. But to reduce these negligible risks even further, DHEA-S may be incorporated in one or more products of the present invention. However, when using DHEA-S as a significant food supplement, increased amounts of cannabinolic compounds may be desired to better enhance digestive uptake. With this caveat, formulations comprising DHEA and DHEA-S may be considered for use interchangeably.

The compositions used in the present invention are preferably formulated and controllably taken administered by or to a human or other mammal to induce desired effects without also inducing undesired side effects, such as undesired anabolic or androgenic effects, in that animal. The delivery of the steroid precursor with minimal activity prior to local processing concomitantly with a cannabinoid to enhance food intake and digestive uptake accomplishes these goals.

Dose will depend on the initial status of circulating hormone, on the active ingredient and its activity within the body, on the size of the person or animal, the frequency of dosing and the rate at which an individual would metabolize the active ingredient(s) of the composition. Thus suitable unit doses may range from about: 0.01 mg to 500 mg, e.g., 0.01 mg, 0.05 mg, 0.07 mg, 0.1 mg, 0.15 mg, 0.2 mg. 0.5 mg, 1.0 mg, 2 mg, 3 mg, 5 mg, 7 mg, 10 mg, 20 mg, 25 mg, 30 mg, 50 mg, 75 mg, 100 mg, 120 mg, 150 mg, 175 mg, 200 mg, 250 mg, 300 mg, 350 mg, 400 mg, 450 mg, or 500 mg. Depending on the route of delivery, the animal's size, the animal's age, the animal's gender, the specific composition, etc. other ranges may be relevant, for example, 10 mg-200 mg, 12.5 mg to 150 mg, 15 mg-100 mg, 20 mg-75 mg, 20 mg-50 mg, or 50 mg-100 mg, etc.

Salts, esters, metabolites, protein bound, glycosylated, or matrixed formats of delivery a can be used in the composition, provided they are converted in vitro or in vivo to an active form. Accordingly, the compositions of the invention may comprise pro-hormone that is bound, covalently or non-covalently to a non-hormonal substance.

The compositions, especially when provided as a food, may optionally include additional vitamins or minerals and scents or flavorings or flavor enhancers to render the composition more acceptable to the individual. For example, vanilla, cinnamon, garlic, coconut, mango, lemon, beef, elk, chicken, salmon and/or other scent or flavor appealing to people, dogs, cats, or other pets may be incorporated, a protein binder and/or a vitamin such as one of the B vitamins, e.g., B6 might be added as it or they might be found to help stabilize hormone level. Vitamin D supplements are suitable vehicles for administering the compositions of the present invention.

The composition may be made available in one or more formats including, but not limited to: a capsule, a tablet, an ampule, a caplet, a liquid beverage, a powder, a liquid or powder beverage additive, a gel, a ready-to-eat food, either moist or dry, a chunk, a bar, a chewable toy of desired shape and size. Dried material may be in form of a powder, scraping, flake, a dusting, a grating, an extrusion, etc. Preparation stages may comprise one or more processes selected from the group consisting of: freeze drying, sonication, freezing, heating, spraying, spray coating, printing, encapsulation, enteric coating, dusting, baking, boiling, frying, steaming, air frying, etc. Coatings may be applied to enhance flavor or smell, for identification, for coloring, etc.

Dried material, freeze dried, oil, spray coated, printed, encapsulated, layered enteric protection, dusted, baked, boiled, broiled, fried, extruded, air fried, steamed, and/or grated ingredients can be prepared with aliquotted amounts of cannabinolic substance and/or prohormone. These will depend on the dosage required and acceptability to the animal and administering human.

A composition of the present invention may further comprise natural and/or artificial flavoring components, dyes or other coloring additives, preservatives and other conventional food supplement additives known in the art to increase palatability, storage options, etc. The inventive composition may comprise multiple layers. For example, a two layered composition may feature a hard or crunchy outer layer that encapsulates a soft or chewy inner layer. Each layer may contain both prohomone and cannabinoid components. Either layer may contain both prohomone and cannabinoid components. Prohormone components may reside in the inner or the outer layer. Cannbinoid components may reside in the inner or outer layer. One of the layers may be present predominantly for flavor, texture, chewyness, salivation promotion, odor, or other desired feature. A third or fourth layer may act as a shell to indicate the content, dosage or strength of the inner composition. A third or fourth layer may serve as a shell or outer coating to facilitate gastronomic appeal. A third or fourth layer may act as a shell to maintain shape of the pellet or chunk. Additional layers are envisioned that may deliver other components and/or stimulate or maintain the animal's interest in ingesting the anti-aging composition. Repeating one or more first, second, third, fourth or higher number layer(s) may deliver a food or supplement with varying tastes or smells as the animal works its way towards the center.

The time and dosage amount administered will vary from individual to individual and will be influenced by the age of the subject, and therefore may be adjusted as an individual ages. In pets, it is believed that generally, the younger the animal, the earlier results will be apparent with a smaller dosage amount needed to achieve optimal results. As the animal ages, the composition will have to be administered perhaps more frequently and in larger dosages for the animal to experience optimal results. For example, in younger animals, the pet owner may feed the animal toe or three times per day with only one or two feedings incorporating a feed or supplement of the present invention. Thus an animal may receive, for example, one, two, or three feeding in accordance with the present invention. When administered as a reward or in a you, administration may occur multiple times per day, presumably in smaller dosages.

The form of the oral composition can be any suitable form that comprises the active ingredient and allows ingestion by the individual. For example, preferably an individual has been under a physician's care and is general good health. However, an individual who is aging can benefit from receiving a therapeutic intervention that while not strictly necessary for life is beneficial though optimizing health, for example, by staving off or diminishing arthritis, other bone issues, such as dysplasia, lessening obesity problems and other issues seen in aging, such as diabetes, lethargy, pain, etc.

Although the androgen in the oral composition may vary, the method of delivery is also an important factor. For example one or more of, DHEA/DHEA-S/7-keto DHEA may be co-administered with an oil, may be admixed in a feed, may be delivered as any convenient ingestible. The format for delivery is subject to choice of the individual, health care professional or vendor and is manageable in accordance with this invention. Animals including humans have shown large variations in efficiencies of moving testosterone and other androgens from the Castro-intestinal track to circulation. Given the beneficial effects of supplementation, most desirable effects being observed with approximately a doubling or tripling of typical circulating steroid, in a middle aged or older mammal, monitoring steroid levels in an individual animal may be a consideration in optimizing dosing.

Cannabinoids may be used serially or coincident with corticosteroid or mitochondrial augmentation or rebalancing. The skilled artisan will be cognizant of the cannabinoid involvement in corticosteroid synthesis and release. When administration of one class is varied, the other classes may benefit from dosage or timing adjustment.

Concluding Comments

Combined interventions involving two or more episodes of redirecting/rebalancing immune/allergy activity, balancing androgen levels in circulation improving animal activity and outlook by optimizing mitochondrial activities will allow even more robust human-animal interaction and better outcomes for the participants. Mitochondrial activities may be simply improved though the cannabinolic component in the composition of the invention which has a dual effect of stimulating appetite and enhancing intestinal uptake of the prohormone.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In the case of conflict, the present specification, including definitions, will control. In addition, the materials, methods, and examples are illustrative only and not intended to be limiting. Although for simplicity in drafting the claims below are drafted in a manner where each dependent claim specifically asserts dependent status with only a single claim, the reader is put on notice that for purpose of disclosure every claim that references a preceding claim also implicitly is understood to have alternate dependency to all claims ultimately depending from the same claim or claims. Of course, the reader will recognize that this implicit understanding will not be stretched ridiculously to the extent that a claim might depend from itself. Other features and advantages of the invention will be apparent from the description and claims of the present specification, referenced materials and the present state of the art.

Examples useful in practicing this invention may include a composition or using a composition that improves a human's or a non-human animal's well-being that may include, contain or comprise an orally or subcutaneously administrable substance having at least one dosage selected from the group consisting of: a mitochondrial booster, an androgen hormone and a prohormone, said dosage selected to optimize at least one physiologic function in a selected mammal. Examples may further feature a compound that has or supports cannabinolic activity perhaps with presence of an endocannabinoid or endocannabinoid mimic substance. Activity of such compound may be effected through a G-protein coupled receptor such as CB1, CB2, TRPV1, TRPV2, TRPV3, TRPV4, TRPA1, TRPM8, GPR18, GPR55, GPR118, and/or GPR119. Anti-oxidant activity may be featured in one or more or the constituents formulated into the product composition.

Cannabinolic activity may reside in, for example, an endogenous mammalian cannabinoid, a phytocannabinoid and/or a synthetic cannabinoid including but not limited to: AEA, 2AG, PEA, OEA, LEA, URB597, URB937, AM374, ARN2508, BIA 10-2474, BMS-469908, CAY-10402, JNJ-245, JNJ-1661010, JNJ-28833155, JNJ-40413269, JNJ-42119779, JNJ-42165279, LY-2183240, Cannabidiol, MK-3168, MK-4409, MM-433593, OL-92, OL-135, PF-622, PF-750, PF-3845, PF-04457845, PF-04862853, RN-450, SA-47, SA-73, SSR-411298, ST-4068, TK-25, URB524, URB597 (KDS-4103), URB694, URB937, VER-156084, V-158866, AM3506, AM6701, CAY10435, CAY10499, IDFP, JJKK-048, JNJ-40355003, JNJ-5003, JW618, JW651, JZL184, JZL195, JZP-372A, KML29, MAFP, MJN110, ML30, N-arachidonoyl maleimide, OL-135, OL92, PF-04457845, SA-57, ST4070, URB880, URB937, indomethacin, MK-886, resveratrol, cis-resveratrol, aspirin, COX-1 inhibitor II, loganin, tenidap, SC560, FR 122047 hydrochloride, valeryl salicylate, FR122047 hydrate, ibuprofen, TFAP, 6-methoxy-2-naphthylacetic acid, meloxicam, APHS, etodolac, meloxicam, meloxicam sodium salt, N-(4-acetamidophenyl)indomethacin amide, N-(2-phenylethyl)indomethacin amide, N-(3-pyridyl)indomethacin amide, indomethacin heptyl ester, SC236, sulinac, sulindac sulfide, pravadoline, naproxen, naproxen sodium salt, meclofenamate sodium, ibuprofen, S-ibuprofen, piroxicam, ketoprofen, S-ketoprofen, R-ibuprofen, Ebselen, ETYA, diclofenac, diclofenac diethylamine, flurbiprofen, fexofenadine, Pterostilbene, Pterocarpus marsupium, 9,12-octadecadiynoic acid, Ketorolac (tromethamine salt), NO-indomethacin, S-flurbiprofen, sedanolide, green tea extract (e.g., epicatechin), licofelone, lornoxicam, rac ibuprofen-d3, ampirxicam, zaltoprofen, 7-(trifluoromethyl) 1H-indole-2,3-dione, aceclofenac, acetylsalicylic acid-d4, S-ibuprofen lysinate, loxoprofen, CAY10589, ZLJ-6, isoicam, dipyrone, YS121, MEG (mercaptoethylguanidine), etc.

Such cannabinoids may be identified as members of a class such as: cannabigerol class, cannabichromene class, cannabicyclol class, $\Delta^8$-tetrahydrocannabinol class, cannabieson class, cannabinol and cannabinodiol class, cannabitriol class and miscellaneous class.

Popular compositions used to practice the invention may include one or more cannabinoids selected from the group consisting of: CBGA, CBGAM, CBG, CBGM; CBGVA, CBGV, CBCA, CBC, CBCVA, CBCV, CBDA, CBD, CBDM, CBD-C4, CBDVA, CBDV, CBD-C1, THCA-A, THCA-B, 6a, 10a-trans-6a, 7,8,10a-tetrahydro-6,6,9-trimethyl-3-pentyl-6H-dibenzo[b,d]pyran-1-ol, THC,) THCA-C4, THC-C4, THCVA, THCV, $\Delta^7$-cis-isotetrahydrocannabivarin, THCA-C1, THC-C1, $\Delta^8$-TCA, $\Delta^8$-THC, CBL, CBLA, CBLV, CBEA-A, CBEA-B, CBE, CBNA, CBN, CBNM, CBN-C4, CBV, CBN-C2, CBN-C1), CBND, CBDV, CBT, 10-EHDT, 8,9-DHDT, CBTV, CBTVE, DCBF, CBF, CBCN, CBT, OTHC, cis-THC, 2H-iso-HHCV, CBR and triOH-THC.

Some practices of the invention can feature metabolism directive or accessory compounds or metabolically active compounds including, but not limited to: an FAAH inhibitor, R-WIN 55,212-2, a MAGL inhibitor, an EFA, oxytocin, ω-3 fatty acid, ω-6 fatty acid.

Some formulations may feature, for example, N-alkylamides, phytoalkanes, n-alkanes, N-acylethanolamines, flavonoids, curcuminoids, polyphenols, biphenyl neolignans, sesquiterpenes, N-Isobutylamides and/or p-hydroxyphenyl-O-arylcarbamates, whose carbon presence in the molecule of interest may be specific or in a range where each molecule comprises from 9 to 39 carbon atoms, for example, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 and/or 39 C/molecule.

Carbon chains may include branches with preferred compounds expected to feature 2-methyl-, 3-methyl-, and dimethyl attachments. Nonacosane, heptacosane, 2,6-dimethyltetradecane, pentacosane, hexacosane, and hentriacontane are examples of useful carbon chains.

Phyto molecules are featured in some embodiments of this invention. A composition may thus feature parts or extracts, for example, of one of more sources derived from *Echinacea, Echinacea purpurea, Echinacea angustifolia*, curcurmin, *Salvia divinorum*, sage, lemon grass, hops, verbana, *Cannabis*, thyme, mango, *Helichrysum umbraculigerum* liverwort, cacao, ginger, tumeric, *Curcuma longa, Magnolia officinalis*, Norway spruce, black pepper, basil, *Myristica fragrans*, cloves, *Sciadopitys verticillata*, oregano, cinnamon, black pepper, hemp, rosemary, flax, *Elettaria repens*, etc.

Phyto- or phyto mimic compounds/molecules may include but are not limited to: abinene, α-pinene, 4,8-dimethyl-1,7-nonadien-4-ol, 2-hydroxy-4-methyl-valeric, acid, methyl, ester, octanal, O-cymene, eucalyptol, α-phellandrene, cis-sabinene, hydroxide, myrcenol, terpinen-4-ol, α-terpineol, β-thujene, ç-terpinene, trans-α-ocimene, carveol, β-citral, guanidine, geraniol, bornyl, acetate, β-pinene, thymol, geranic, acid, methyl, ester, β-terpinyl, acetate, d-limonene, eugenol, geranyl, acetate, dihydrocarvyl, acetate, α-ylangene, cis-dodec-5-enal, 3-phenyl-2-propenoic, acid, methyl, ester, β-elemene, c, vanillin, epoxy-α-terpenyl, acetate, butanoic, acid, 2-methyl-, 3,7-dimethyl-2,6-octadienyl, ester, 1-methyl-4-(1-acetoxy-1-methylethyl)-cyclohex-2-enol, 1,2,3,4,4a,5,6,8a-octahydro-4a,8-dimethyl-2-(1-methylethenyl)-, [2r-(2à, 4aà,8aá)]-naphthalene, p-mentha-1(7),8-dien-2-ol, ç-muurolene, hydroxy-α-terpenyl, acetate, nerolidol, geranyl, bromide, (−)-α-panasinsen, pyrocatechol, ç-elemene, 9,10-dehydro-isolongifolene, à-calacorene, cis-verbenol, acetic, acid, 1-methyl-1-(4-methyl-5-oxo-cyclohex-3-enyl)ethyl, ester, alloaromadendrene, z,z-2,6-dimethyl-3,5,7-octatriene-2-ol, 4-epi-cubedol, 2-oxabicyclo[2.2.2]octan-6-ol, 1,3,3-trimethyl-acetate, patchoulane, farnesol, caryophyllene, oxide, cis-lanceol, ledene, oxide-(ii), farnesol, acetate, 6-epi-shyobunol, falcarinol, phytol, aromadendrene, oxide-(2), heptacosane, longipinene, epoxide, hentriacontane, decamethyl-cyclopentasiloxane, geranyl, isobutyr, hexamethyl-cyclotrisiloxane, 1-docosene, tetratetracontane, dodecamethyl-cyclohexasiloxane, etc.

Supplemental components used to modify or to improve more rudimentary formulations or compositions may comprise, but are not limited to: β-caryophyllene, a β-caryophyllene oxide, salvinorin A, myrcene, perrottetinenic acid, apigenin, quercetin, cannflavin A, cannflavin B, β-sitosterol, vitexin, isovitexin, kaempferol, luteolin, orientin, a gingerol, capsaicin, curcumin, demethoxycurcumin, bisdemethoxycurcumin, cyclocurcumin, trans-resveratrol, diferuloylmethane, trans-arachidins, trans-piceatannol, isoprenylated trans-resveratrol derivatives, sciadonic acid magnolol, honokiol, malyngamide B, (+) sabinene, (−) sabinene, Isobutylamide, dodeca-2E,4E-dienoic acid isobutylamide, dodeca-2E,4E,8Z, 10Z-tetraenoic acid alkylamide, 1-[(2E,4E,8Z)-tetradecatrienoyl] piperidine, β-caryophyllene, ajulemic acid, etc.

Compositions are not limited to classic medicament shapes or formats. For example, a gel, a powder, a toy, a liquid, a food supplement, a moist food, a dry food, a small treat, a solidified matrix, etc., may be used for delivery. A 3-D printer may be applied to control dosing of the featured components, e.g., a hormone or prohormone, Delayed-release shaped constructs, a chewable toy-shaped substance, e.g., a dogie bone, a dinosaur, a cat, a mouse, a squirrel, a rodent, a ring, a fist, a bow, a ball, etc. One or more formats may feature a plurality of packaging, wherein at least a first packaging contains active ingredient for admixing to at least a second package contents.

The invention claimed is:

1. A composition comprising >1.0 mg of an androgenic prohormone and >0.5 mg of a compound that binds and stimulates a mammalian endocannabinoid receptor.

2. The composition of claim 1 said prohormone is selected from the group consisting of: DHEA, 7-keto DHEA and DHEA-S.

3. The composition of claim 1 wherein said endogenous endocannabinoid receptor is selected from the group consisting of: CB1, CB2, TRPV1, TRPV2, TRPV3, TRPV4, TRPA1, TRPM8, GPR18, GPR119, GPR55, GPR118 and analogues thereto.

4. The composition of claim 1 wherein said compound that binds and stimulates a mammalian endocannabinoid receptor comprises a member of a class selected from the group consisting of: cannabigerol class, cannabichromene class, cannabicyclol class, $\Delta^8$-tetrahydrocannabinol class, cannabieson class, cannabinol and cannabinodiol class, cannabitriol class, and miscellaneous class.

5. The composition of claim 4 wherein said compound that binds and stimulates a mammalian endocannabinoid receptor comprises a member of the cannabinol and cannabinodiol class.

6. The composition of claim 4 wherein said compound that binds and stimulates a mammalian endocannabinoid receptor comprises a member of the Cannabichromene class.

7. The composition of claim 6 wherein said compound that binds and stimulates a mammalian endocannabinoid receptor comprises a compound selected from the group consisting of: cannabidiolic acid (CBDA), cannabidiol (CBD), cannabidiol monomethylether (CBDM), cannabidiol C4 (CBD-C4), and cannabidivarinic acid (CBDVA).

8. The composition of claim 1 further comprising an oil selected from the group consisting of: vegetable, rapeseed/canola, soy, corn, peppermint, lavender, sandalwood, bergamot, rose, chamomile, ylang-ylang, tea tree, myrcene/hops, jasmine, and lemon.

9. The composition of claim 1 further comprising nutmeg or nutmeg extract.

10. The composition of claim 1 formulated as an oral preparation selected from the group consisting of: a food, a toothpaste, a spritz, a snack, a food supplement, a reward, a spray, an ampule, a chewable edible, a supplemented rawhide, a vitamin D supplement, and a chew toy.

11. The composition of claim 10 wherein ingesting or feeding said composition to an animal results in increased activity.

12. The composition of claim 1 formulated as a feed supplement, said supplement in a format selected from the group consisting of: a gel, a powder, a liquid, a grating, a strip, an ampule, a tablet, and a capsule.

13. The composition of claim 1 comprising an outer coating that crunches when crushed to release a soft encapsulated portion.

14. The composition of claim 13 wherein said encapsulated portion comprises a compound that binds and stimulates a mammalian endocannabinoid receptor.

15. The composition of claim 13 wherein said encapsulated portion comprises an androgenic prohormone.

16. The composition of claim 13 wherein outer coating that crunches comprises a compound that binds and stimulates a mammalian endocannabinoid receptor.

17. The composition of claim 13 wherein outer coating that crunches comprises an androgenic prohormone.

18. The composition of claim 13 wherein outer coating that crunches comprises an androgenic prohormone.

19. The composition of claim 1 further comprising an outer coating that serves as a marker or label identifying the composition.

20. A method for providing an anti-aging composition to a canine, said method comprising delivering to a canine the composition of claim 1.

21. A method of making the composition of claim 1 comprising spraying a mist comprising said compound that binds and stimulates a mammalian endocannabinoid receptor onto a food or food supplement comprising said androgenic prohormone.

* * * * *